United States Patent [19]

Caprathe et al.

[11] Patent Number: 5,120,748
[45] Date of Patent: Jun. 9, 1992

[54] SUBSTITUTED 1,2,3,6-TETRAHYDROPYRIDINES AS CENTRAL NERVOUS SYSTEM AGENTS

[75] Inventors: Bradley W. Caprathe, Redford; Juan C. Jaen, Plymouth; Lawrence D. Wise, Ann Arbor, all of Mich.

[73] Assignee: Warner-Lambert Company, Morris Plains, N.J.

[21] Appl. No.: 722,981

[22] Filed: Jun. 28, 1991

[51] Int. Cl.$^5$ .................. A61K 31/44; C07D 409/14
[52] U.S. Cl. .................. 514/334; 514/252; 514/269; 514/274; 514/333; 544/310; 544/316; 544/319; 544/333; 544/405; 546/256; 546/257; 546/258; 546/266
[58] Field of Search .......... 514/334, 333, 252, 269, 514/274; 544/310, 316, 319, 333, 405; 546/255, 256, 257, 258, 266

[56] References Cited

U.S. PATENT DOCUMENTS

| | | | |
|---|---|---|---|
| 4,617,309 | 10/1986 | Bottcher et al. | 546/273 |
| 4,743,692 | 5/1988 | Teller et al. | 546/256 |
| 4,870,087 | 9/1989 | Gottschlich et al. | 546/273 |
| 4,942,169 | 7/1990 | Sugimoto et al. | 546/176 |
| 5,045,550 | 9/1991 | Jaen et al. | 514/332 |

Primary Examiner—C. Warren Ivy
Assistant Examiner—James H. Turnipseed
Attorney, Agent, or Firm—Francis J. Tinney

[57] ABSTRACT

Substituted 1,2,3,6-tetrahydropyridines are described, as well as methods for the preparation and pharmaceutical composition of same, which are useful as central nervous system agents and are particularly useful as dopaminergic, antipsychotic, and antihypertensive agents as well as for treating hyperprolactinaemia-related conditions and central nervous system disorders.

6 Claims, No Drawings

SUBSTITUTED 1,2,3,6-TETRAHYDROPYRIDINES AS CENTRAL NERVOUS SYSTEM AGENTS

BACKGROUND OF INFORMATION

The present invention relates to novel substituted 1,2,3,6-tetrahydropyridines useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents.

A series of 4-thienyl-1,2,3,6 tetrahydropyridines of the Formula I

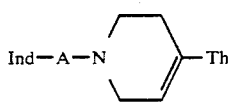

in which Ind is a 3-indolyl radical which can be substituted once or twice by alkyl, O-alkyl, S-alkyl, SO-alkyl, SO$_2$-alkyl, OH, F, Cl, Br, CF$_3$ and/or CN or by a methylenedioxy group, A is —(CH$_2$)$_4$— or —CH—$_2$—L—CH$_2$CH$_2$—, L is —S—, —SO— or SO$_2$—, and Th is a 2- or 3-thienyl radical, and in which the alkyl groups each have one to four carbon atoms, and their physiologically acceptable acid addition salts, having dopamine stimulating effects on the central nervous system, is disclosed in U.S. Pat. No. 4,870,087.

A series of sulfur-containing indole derivatives of the Formula I

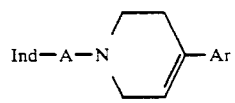

wherein Ind is a 3-indolyl radical which can be substituted once or twice by alkyl, O-alkyl, S-alkyl, SO-alkyl, SO$_2$-alkyl, OH, F, Cl, Br, CF$_3$ and/or CN or by a methylenedioxy group, A is —(CH$_2$)$_n$—E—C$_m$H$_{2m}$— or —(CH$_2$)$_n$—E—C$_{m-1}$H$_{2m-2}$CO—, n is 0 or 1, m is 2, 3 or 4, E is S, SO or SC$_2$ and Ar is a phenyl group which is unsubstituted or substituted once or twice by alkyl, O-alkyl, S-alkyl, SO-alkyl, SO$_2$-alkyl, OH, F, Cl, Br, CF$_3$ and/or CN or by a methylenedioxy group and wherein the alkyl groups have one to four carbon atoms, and their physiologically acceptable acid addition salts having dopamine stimulating effects on the central nervous system is disclosed in U.S. Pat. No. 4,617,309.

However, the compounds disclosed in the aforementioned references do not disclose or suggest the combination of structural variations of the compounds of the present invention described hereinafter.

SUMMARY OF THE INVENTION

Accordingly, the present invention is a compound of Formula I

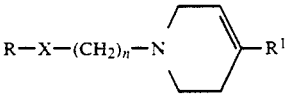

wherein R is

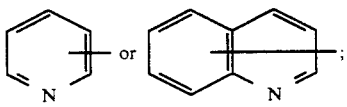

X is —CH$_2$—S(O)$_m$— wherein m is zero or an integer of 1 or 2, or —S(O)$_m$—CH$_2$— wherein m is as defined above;

n is an integer of 2,3, or 4;

R$^1$ is aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen; and corresponding isomers thereof; or a pharmaceutically acceptable acid addition salt thereof.

As dopaminergic agents, the compounds of Formula I are useful as antipsychotic agents for treating psychoses such as schizophrenia. They are also useful as antihypertensive agents and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec butyl, isobutyl, tert-butyl, n-pentyl, n-hexyl, and the like.

The term "aryl" means an aromatic radical which is a phenyl group or phenyl group substituted by one to four substituents selected from lower alkyl, lower alkoxy, lower thioalkoxy, halogen or trifluoromethyl such as, for example, phenyl, para-fluoro phenyl, and the like.

"Lower alkoxy" and "thioalkoxy" are O-alkyl or S-alkyl of from one to six carbon atoms as defined above for "lower alkyl."

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1–19, (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention (compounds wherein m is 1) possess asymmetric carbon atoms (optical centers); the racemates as well as the individual enantiomers are intended to be encompassed within the scope of the present invention.

A preferred compound of Formula I is one wherein R is

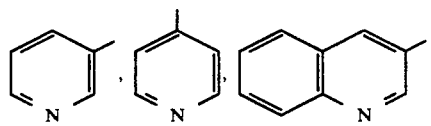

-continued

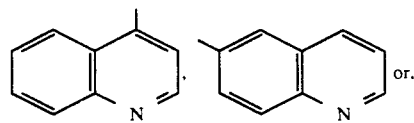

X is —CH$_2$—S—, or —S—CH$_2$—;
n is an integer of 2 or 3;
R$^1$ is aryl, 2- or 3-thienyl, or 2- or 3-thienyl substituted by lower alkyl or halogen.

Another preferred embodiment is a compound of Formula I wherein

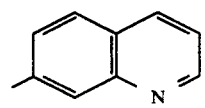

X is —CH$_2$—S—, or —S—CH$_2$—;
n is an integer of 2 or 3;
R$^1$ is aryl, 2- or 3-thienyl, or 2- or 3-thienyl substituted by lower alkyl or halogen. Particularly valuable are:

3-[[[2-(1,2,3,6-Tetrahydro-4-phenyl-1-pyridinyl)-ethyl]-thio]methyl]pyridine, dihydrochloride;

4-[[3-[3,6-Dihydro-4-(2-thienyl)-1(2H)-pyridinyl]-propyl]thio]pyridine;

4-[[3-(3,6-Dihydro-4-phenyl-1(2H)-pyridinyl)-propyl]thio]pyridine;

1,2,3,6-Tetrahydro-4-phenyl-1-[4-(4-pyridinyl-thio)-butyl]pyridine and 1,2,3,6 tetrahydro-1-[4-(4-pyridinylthio)butyl]-4-(2 thienyl)pyridine, dihydrochloride; or a pharmaceutically acceptable acid addition salt thereof.

The compounds of Formula I are valuable dopaminergic agents. The tests employed indicate that compounds of Formula I possess dopaminergic activity. Thus, the compounds of Formula I were tested for their ability to inhibit locomotor activity in mice according to the assay described by J. R. McLean, et al, *Pharmacology, Biochemistry and Behavior*, Volume 8, pages 97–99 (1978); for their ability to inhibit [$^3$H]-spiroperidol binding in a receptor assay described by D. Griogoriadis and P. Seeman, *Journal of Neurochemistry*, Volume 44, pages 1925–1935 (1985); and for their ability to inhibit dopamine synthesis in rats according to the protocol described by J. R. Walters and R. H. Roth, *Naunyn-Schmiedeberg's Archives of Pharmacology*, Volume 296, pages 5–14 (1976). The above test methods are incorporated herein by reference. The data in the table show the dopaminergic activity of representative compounds of Formula I.

TABLE 1

Biological Activity of Compounds of Formula I

| Example Number | Compound | Inhibition of Locomotor Activity in Mice $ED_{50}$, mg/kg, IP | % Reversal of Brain Dopamine Synthesis in Rats at 10 mg/kg. IP | Inhibition of [$^3$H]Spiroperidol Binding $IC_{50}$, μM |
|---|---|---|---|---|
| 1 | 3-[[[2-(1,2,3,6-Tetrahydro-4-phenyl-1-pyridinyl)ethyl]thio]methyl]pyridine, dihydrochloride | 0.18 | 70 | |
| 2 | 4-[[3-[3,6-Dihydro-4-(2-thienyl)-1(2H)-pyridinyl]propyl]thio]pyridine | 0.5 | | 86 |
| 3 | 4-[[3-(3,6-Dihydro-4-phenyl-1(2H)-pyridinyl)propyl]thio]pyridine | 0.4 | 48 | 46 |
| 4 | 1,2,3,6-Tetrahydro-4-phenyl-1-[4-(4-pyridinylthio)butyl]pyridine | 1.0 | 82 | 92 |
| 5 | 1,2,3,6-Tetrahydro-1-[4-(4-pyridinylthio)butyl]-4-(2-thienyl)pyridine, dihydrochloride | 1.8 | 47 | 190 |

A compound of Formula Ia

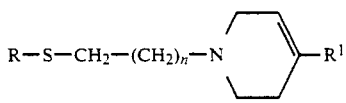

wherein R is

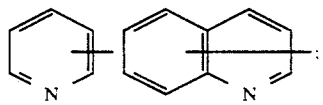

or n is an integer of 2, 3, or 4;

R$^2$ is aryl, 2-, 3 , or 4-pyridinyl or 2-, 3-, or 4-pyridinyl substituted by lower alkyl, lower alkoxy, or halogen, 2 , 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2 or 3-thienyl or 2- or 3-thienyl substituted by lower alkyl or halogen, 2- or 3-furanyl or 2 or 3-furanyl substituted by lower alkyl or halogen, 2-, 4-, or 5-thiazolyl or 2-, 4-, or 5-thiazolyl substituted by lower alkyl or halogen; and corresponding isomers thereof; or a pharmaceutically acceptable acid addition salt thereof may be prepared by reacting a compound of Formula II

wherein L is a leaving group such as, for example, halogen such as bromo, chloro, iodo, and the like or paratoluenesulfonyloxy and the like and R and n are as defined above with a compound of Formula III

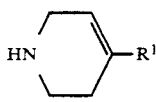

wherein R$^1$ is as defined above in the presence of a base such as, for example, an alkali metal or alkaline-earth metal carbonate or bicarbonate such as sodium carbonate, potassium carbonate, sodium bicarbonate, potassium bicarbonate and the like in a solvent such as, for example, dimethylformamide and the like at about 25° C. to about the reflux temperature of the solvent for about 1 hour to about 24 hours to afford a compound of Formula Ia. Preferably, the reaction is carried out in the presence of sodium bicarbonate in dimethylformamide at about 80° C. for about 14 hours.

A compound of Formula Ib

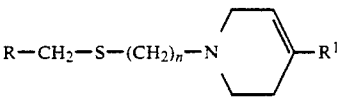

wherein R, n and R$^1$ are as defined above may be prepared by reacting a compound of Formula IV

wherein R, n and L are as defined above with a compound of Formula III using the methodology used to prepare a compound of Formula Ia from a compound of Formula II and a compound of Formula III to afford a compound of Formula Ib. Alternatively, a compound of Formula Ib may be prepared by reacting a compound of Formula V

wherein R is as defined above with a compound of Formula VI

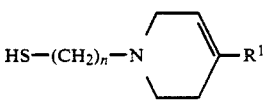

wherein R$^1$ and n are as defined above in the presence of a base such as, for example, triethylamine and the like in a solvent such as, for example, dimethylformamide, acetonitrile and the like at about 25° C. to about the reflux temperature of the solvent for about one hour to about 24 hours to afford a compound of Formula Ib. Preferably, the reaction is carried out in the presence of triethylamine in dimethylformamide at about 80° C. for about 8 hours.

A compound of Formula Ic

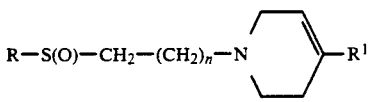

wherein R, R$^1$ and n are as defined above may be prepared by reacting a compound of Formula Ia with an oxidizing reagent such as, for example, hydrogen peroxide and the like in a solvent such as, for example, ethanol and the like at about the reflux temperature of the solvent for about 8 hours to afford a compound of Formula Ic. Preferably, the reaction is carried out with 30% hydrogen peroxide in ethanol at about reflux for about 8 hours.

A compound of Formula Id

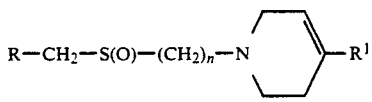

wherein R, R$^1$ and n are as defined above may be prepared from a compound of Formula Ib using the methodology used to prepare a compound of Formula Ic from a compound of Formula Ia to afford a compound of Formula Id.

Preferably, optically active sulfoxides of Formula I designated Formulas Ic-1, Ic-2, Id-1 and Id-2 may be prepared as outlined in Scheme I. Thus, a compound of Formula X wherein R is as defined above is reacted with a compound of Formula IX wherein R*—OH is an optically active alcohol such as, for example, (—)menthol and the like to afford a compound of Formula VIII wherein R and R* are as defined above as a mixture of diastereomers. The diastereomers of Formula VIII are subsequently separated using conventional methodology such as, for example, chromatography and the like to afford a compound of Formula VIIIa and a compound of Formula VIIIb wherein R and R* are as defined above. Reaction of either a compound of Formula VIIIa or a compound of Formula VIIIb with a compound of Formula VII wherein R$^1$ and n are as defined above affords respectively either a compound of Formula Ic-1, or Formula Ic-2. Reaction of a compound of Formula XII wherein R is as defined above with a compound of Formula IX wherein R*-OH is as defined above using the methodology used to prepare a compound of Formula VIII from a compound of Formula X affords a compound of Formula XI wherein R and R* are as defined above. Separation of a compound of Formula XI into a compound of Formula XIa and a compound of Formula XIb and subsequent reaction with a compound of Formula VIIa wherein R$^1$ and n are as defined above using the methodology used to prepare a compound of Formula Ic-1 or Formula Ic-2 from a compound of Formula VII affords either a compound of Formula Id-1 or Formula Id-2.

A compound of Formula Ie

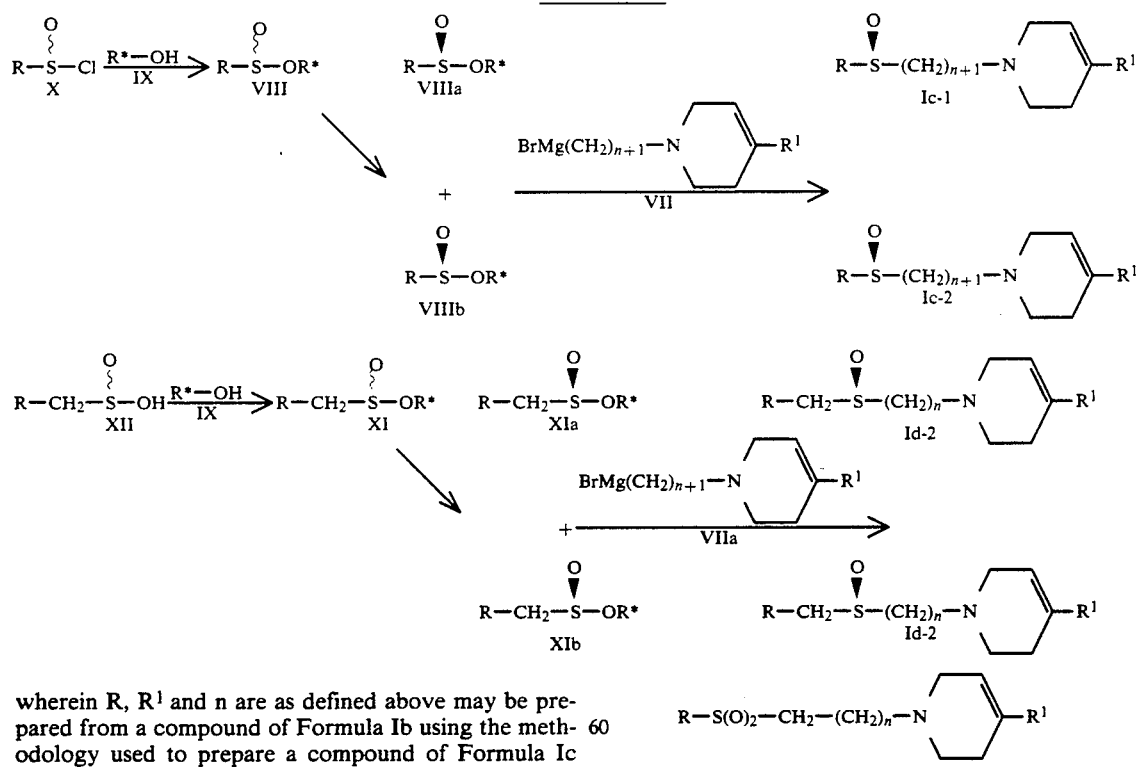

wherein R, R$^1$ and n are as defined above may be prepared by reacting a compound of Formula Ia with an oxidizing reagent such as, for example, hydrogen peroxide and the like in the presence of an organic acid such as, for example, acetic acid and the like at about the reflux temperature of the acid for about 8 hours to afford a compound of Formula Ie. Preferably, the reaction is carried out with 30% hydrogen peroxide in acetic acid at about reflux for about 8 hours.

A compound of Formula If

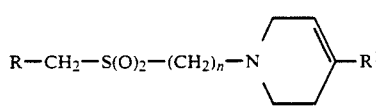

wherein R, $R^1$ and n are as defined above may be prepared from a compound of Formula Ib using the methodology used to prepare a compound of Formula Ie from a compound of Formula Ia to afford a compound of Formula If.

A compound of Formula II wherein R, L and n are as defined above may be prepared from a compound of Formula XIII

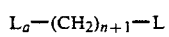

wherein La and L are leaving groups of different reactivity such as, for example, Br and Cl; I and Cl; para-toluenesulfonyloxy and Cl; and the like and n is as defined above and a compound of Formula XIV

wherein R is as defined above in the presence of a base such as, for example, an alkali metal carbonate or bicarbonate such as potassium carbonate, sodium carbonate and the like in a solvent such as, for example, acetone and the like at about 25° C. to about the reflux temperature of the solvent for about 30 minutes to about 24 hours to afford a compound of Formula II. Preferably, the reaction is carried out in the presence of potassium carbonate in acetone at about reflux for about 1 hour.

A compound of Formula IV wherein R, L and n are as defined above may be prepared from a compound of Formula XV

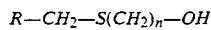

wherein R and n are as defined above by converting the hydroxyl group into a leaving group with, for example, thionyl chloride, thionyl bromide and the like in a solvent such as, for example, chloroform and the like or para-toluenesulfonyl chloride and the like in the presence of a base such as, for example, pyridine and the like to afford a compound of Formula IV.

A compound of Formula XV wherein R and n are as defined above may be prepared from a compound of Formula XVI

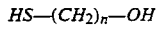

wherein n is as defined above and a compound of Formula XVII

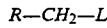

wherein R and L are as defined above in the presence of a base such as, for example, triethylamine and the like, in a solvent such as, for example, acetonitrile and the like to afford a compound of Formula XV.

A compound of Formula XVII wherein R is as defined above may be prepared from a compound of Formula XVIII

wherein R is as defined above using the methodology used to prepare a compound of Formula IV, from a compound of Formula XV to afford a compound of Formula XVII.

A compound of Formula VI wherein $R^1$ and n are as defined above may be prepared from a compound of Formula XIX

wherein L and n are as defined above and a compound of Formula III in a solvent such as, for example, acetonitrile and the like to afford a compound of Formula VI. Alternatively, a compound of Formula VI may be prepared from a compound of Formula XX

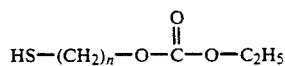

wherein n is as defined above and a compound of Formula III in a solvent such as, for example, toluene and the like to afford a compound of Formula VI.

A compound of either Formula VII or Formula VIIa wherein $R^1$ and n are as defined may be prepared from either a compound of Formula XXI or Formula XXIa, respectively

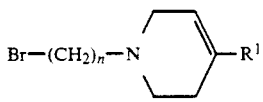

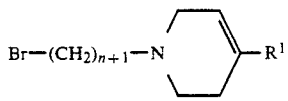

wherein $R^1$ and n are as defined above in the presence of magnesium and a solvent such as, for example, diethyl ether and the like to afford either a compound of Formula VII or Formula VIIa, respectively.

A compound of either Formula XXI or Formula XXIa wherein $R^1$ and n are as defined above may be prepared from either a compound of Formula XXII or Formula XXIIa

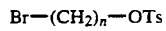

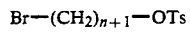

wherein Ts is para-toluenesulfonyl and n is as defined above and a compound of Formula III to afford either a compound of Formula XXI or Formula XXIa, respectively.

Compounds of Formula III, Formula V, Formula IX, Formula X, Formula XII, Formula XIII, Formula XIV, Formula XVI, Formula XVIII, Formula XIX and Formula XX are either known or capable of being prepared by methods known in the art.

Additionally, a compound of Formula I (wherein m is 1), which is a racemic mixture, may be further resolved into its enantiomers. Accordingly, as another aspect of the present invention, a compound of Formula (±)I (wherein m is 1) may be resolved into its enantiomers by the use of conventional methodology such as, for example, optically active acids. Thus, the resulting diastereomeric salts may be separated by crystallization and then converted by conventional methodology to the optically active enantiomer (+)I or (−)I (wherein m is 1).

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day is desired.

The following nonlimiting examples illustrate the inventors' preferred methods for preparing the compounds of the invention.

EXAMPLE 1

3-[[[2-(1,2,3,6 Tetrahydro-4-phenyl 1-pyridinyl)ethyl]thio]methyl]pyridine, dihydrochloride A solution of 3-picolyl chloride hydrochloride (2.50 g) and 3,6-dihydro-4-phenyl-1(2H)-pyridineethanethiol hydrochloride (3.90 g) (Example A) in 100 mL of dimethylformamide is treated with triethylamine (7.4 ml) and the mixture is heated at 80° C. for 8 hours. The solvent is evaporated in vacuo, and the residue is partitioned into chloroform/sodium bicarbonate solution. The organic extract is dried over magnesium sulfate, filtered and concentrated. The crude product is purified by column chromatography (silica gel; 2% methanol in chloroform) to yield 1.7 g of the title compound as an oil, which is converted into its hydrochloride salt (hydrogen chloride gas in diethyl ether) and recrystallized from ethanol/acetonitrile; mp 218°–220° C. (dec).

EXAMPLE 2

4-]]3-]3,6-Dihydro 4-(2 -thienyl)-1(2H)-pyridinyl]propyl]thio]pyridine

A mixture of 4-(3-chloropropylthio)pyridine (2.2 g) (Example B), 3,6-dihydro-4-(2-thienyl)-1(2H)-pyridine hydrochloride (3.54 g) and sodium bicarbonate (5.0 g) in 20 ml of dimethylformamide is heated at 80° C. under nitrogen for 14 hours. The mixture is concentrated in vacuo and the residue is partitioned into chloroform/water. The organic extract is dried over magnesium sulfate and concentrated. The crude product is purified by column chromatography (silica; 2% to 5% methanol in chloroform) to give 2.34 g of the title compound as a solid; mp 86°-87° C.

In a process analogous to Example 2 using appropriate starting materials, the corresponding compounds (Examples 3 to 5) of Formula I are prepared as follows:

EXAMPLE 3

4-[[3-(3,6-Dihydro-4-phenyl-1(2H)-pyridinyl)propyl]thio]pyridine; mp 93°-95° C.

EXAMPLE 4

1,2,3,6-Tetrahydro-4-phenyl-1-[4-(4-pyridinylthio)butyl]pyridine; mp 57°-60° C.

EXAMPLE 5

1,2,3,6-Tetrahydro-1-[4-(4-pyridinylthio)butyl]-4-(2-thienyl)pyridine, dihydrochloride; mp 214°-217° C.

PREPARATION OF STARTING MATERIALS

EXAMPLE A 3,6-Dihydro-4-phenyl-1(2H) pyridineethanethiol

4-Phenyl-1,2,3,6-tetrahydropyridine hydrochloride (68.1g) is partitioned between 3N sodium hydroxide and chloroform. The organic extract is dried over magnesium sulfate, filtered and concentrated in vacuo. The residual oil is dissolved in 50 mL toluene and placed in a 3 neck flask fitted with a dry ice condenser and an addition funnel. The flask is placed under a nitrogen atmosphere, and ethyl 2-mercaptoethyl carbonate (26.1 g) is added dropwise. The reaction mixture is refluxed for 4 hours. The solid formed is filtered, washed with cold toluene, and discarded. The filtrate is concentrated and distilled in vacuo to give 24.9 g of the title compound as a light yellow liquid; bp$_{0.3\ mm}$ 134°-150° C., which is converted into a hydrochloride salt; mp 174°-184° C., in a conventional manner.

EXAMPLE B 4-(3-Chloropropylthio)pyridine

A mixture of 4-mercaptopyridine (5.0 g), 1-bromo-3-chloropropane (14.2 g), and anhydrous potassium carbonate in 250 mL acetone is refluxed under nitrogen for 1 hour. The mixture is cooled, filtered and concentrated. The residue is taken up into diethyl ether and washed with brine, dried over magnesium sulfate and evaporated in vacuo. The crude product is purified by column chromatography (silica; hexane: ethyl acetate, 50:50) to give the title compound (7.34 g) as a colorless oil which is used directly in further transformations.

EXAMPLE C 4-(4-Chlorobutylthio)pyridine

Using the procedure of Example B and replacing 1 bromo-3 chloropropane with 1 bromo-4 chlorobutane the title compound is obtained. This compound is converted to the hydrochloride salt; mp 80°-85° C.

We claim:
1. A compound of Formula I

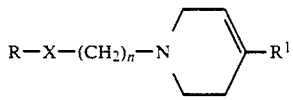

wherein R is

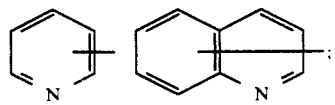

X is —CH$_2$—S(O)$_m$— wherein m is zero or an integer of 1 or 2, or
—S(O)$_m$—CH$_2$— wherein m is as defined above;
n is an integer of 2, 3, or 4;
R$^1$ is aryl, 2-, 3-, or 4 pyridinyl or 2-, 3-, or 4-pyridinyl substituted by lower alkyl, lower alkoxy, or halogen, 2-, 4-, or 5-pyrimidinyl or 2 , 4-, or 5 pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5 thiazolyl substituted by lower alkyl or halogen; and corresponding isomers thereof; or a pharmaceutically acceptable acid addition salt thereof.
2. A compound according to claim 1, in which

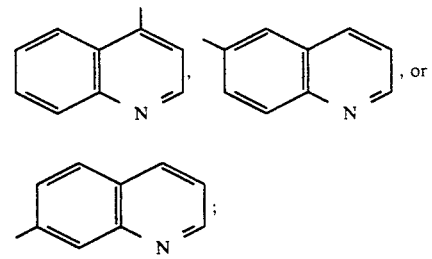

X is —CH$_2$—S—, or —S—CH$_2$—;
n is an integer of 2 or 3;
R$^1$ is aryl, 2- or 3-thienyl, or 2- or 3-thienyl substituted by lower alkyl or halogen.
3. A compound according to claim 2, in which

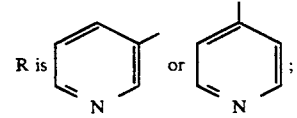

X is —CH$_2$—S—, or —S—CH$_2$—;
n is an integer of 2 or 3;
R$^1$ is aryl, 2- or 3-thienyl, or 2- or 3 thienyl substituted by lower alkyl or halogen.
4. A compound according to claim 3 selected from the group consisting of
3-[[[2-(1,2,3,6 Tetrahydro-4-phenyl-1-pyridinyl)ethyl]thio]methyl]pyridine, dihydrochloride;
4-[[3-[3,6-Dihydro-4-(2-thienyl)-1(2H)-pyridinyl]propyl]thio]pyridine;

4-[[3-(3,6-Dihydro-4-phenyl-1(2H)-pyridinyl)-propyl]thio]pyridine;

1,2,3,6-Tetrahydro-4-phenyl-1-[4-(4-pyridinylthio)-butyl]pyridine; and 1,2,3,6-Tetrahydro-1-[4-(4-pyridinylthio)-butyl]-4 (2-thienyl)pyridine dihydrochloride.

5. A method of treating schizophrenia comprising administering to a host suffering therefrom a therapeutic effective amount of a compound according to claim 1 in unit dosage form.

6. A pharmaceutical composition adapted for administration as a dopaminergic, antipsychotic, antihypertensive or antidepressant agent comprising a therapeutic effective amount of a compound according to claim 1 in admixture with a pharmaceutically acceptable excipient, diluent or carrier.

* * * * *

UNITED STATES PATENT AND TRADEMARK OFFICE
CERTIFICATE OF CORRECTION

PATENT NO. : 5,120,748
DATED : June 9, 1992
INVENTOR(S) : Caprathe, et al

Page 1 of 2

It is certified that error appears in the above-indentified patent and that said Letters Patent is hereby corrected as shown below:

In Column 14, line 10, delete " 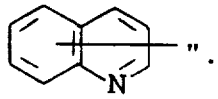 ".

In Column 14, line 34, insert -- R is , or  --.

In Column 14, line 65, insert -- — -- before Tetrahydro.

UNITED STATES PATENT AND TRADEMARK OFFICE
CERTIFICATE OF CORRECTION

PATENT NO. : 5,120,748
DATED : June 9, 1992
INVENTOR(S) : Caprathe, et al

It is certified that error appears in the above-indentified patent and that said Letters Patent is hereby corrected as shown below:

In Column 14, lines 35 to 40, delete:

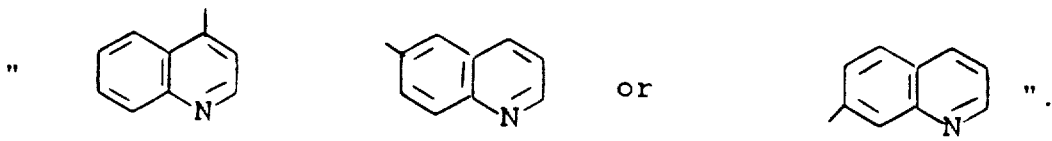

Signed and Sealed this

Twenty-fourth Day of August, 1993

BRUCE LEHMAN

Attest:

Attesting Officer

Commissioner of Patents and Trademarks